United States Patent [19]

Dragan et al.

[11] Patent Number: 5,125,836

[45] Date of Patent: Jun. 30, 1992

[54] EASY LOADING MANUAL EXTRUDER FOR VISCOUS MATERIAL

[75] Inventors: William B. Dragan, Easton; John Discko, Jr., Hamden, both of Conn.

[73] Assignee: Centrix, Inc., Milford, Conn.

[21] Appl. No.: 650,100

[22] Filed: Feb. 4, 1991

[51] Int. Cl.⁵ .................................................. A61C 5/04
[52] U.S. Cl. .................................................. 433/90
[58] Field of Search ........................... 433/90, 89, 80

[56] References Cited

U.S. PATENT DOCUMENTS

| | | | |
|---|---|---|---|
| 2,505,028 | 4/1950 | Boeger | 433/90 |
| 4,384,853 | 5/1983 | Welsh | 433/90 |

Primary Examiner—John J. Wilson
Attorney, Agent, or Firm—Paul A. Fattibene; Arthur T. Fattibene

[57] ABSTRACT

A manual extruder or syringe having a longitudinal slot therein adjacent the full circumference front end for receiving the nozzle of a cartridge. A barrel of a syringe having a front end and a breach opening adjacent thereto for receiving a cartridge of the type having an angularly disposed nozzle and rear flange. The slot in the front end is only wide enough to receive the width of the nozzle and prevents the body portion of the cartridge from passing therethrough. The body portion can then easily be slid along the barrel into the front end to be held by the flange against a substantially full circumference shoulder. The front end can be made very rigid, and the shoulder extending substantially the full circumference of the front end securely holds the cartridge preventing any possibility of unintentional separation from the syringe. In one embodiment, a notch is also provided to permit the cartridge to be inserted with the nozzle pointing upward. In another embodiment, a track or guide is provided along the slot to help guide the body portion of the cartridge past the shoulder.

12 Claims, 3 Drawing Sheets

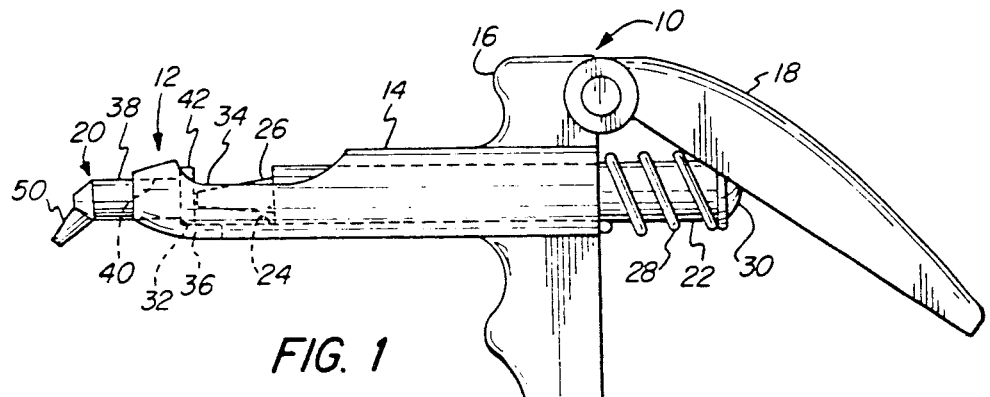
FIG. 1
FIG. 2
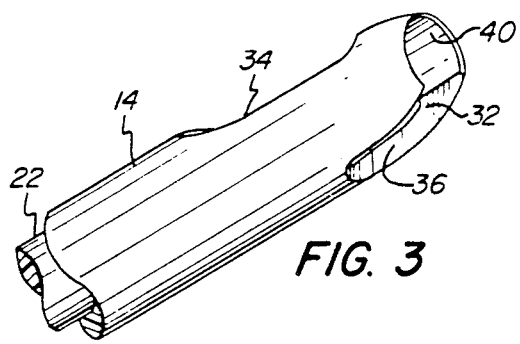
FIG. 3
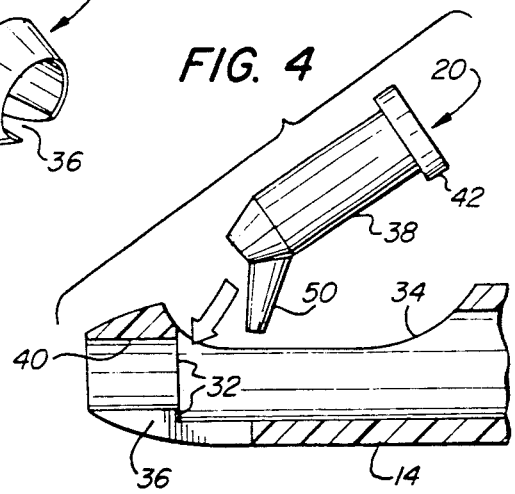
FIG. 4
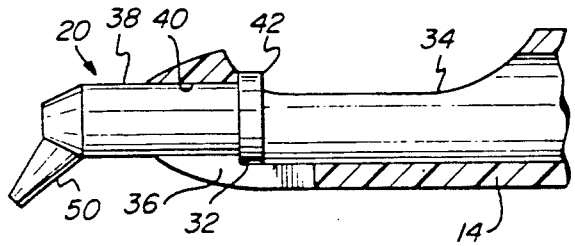
FIG. 6
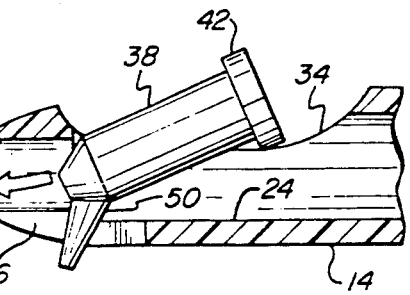
FIG. 5

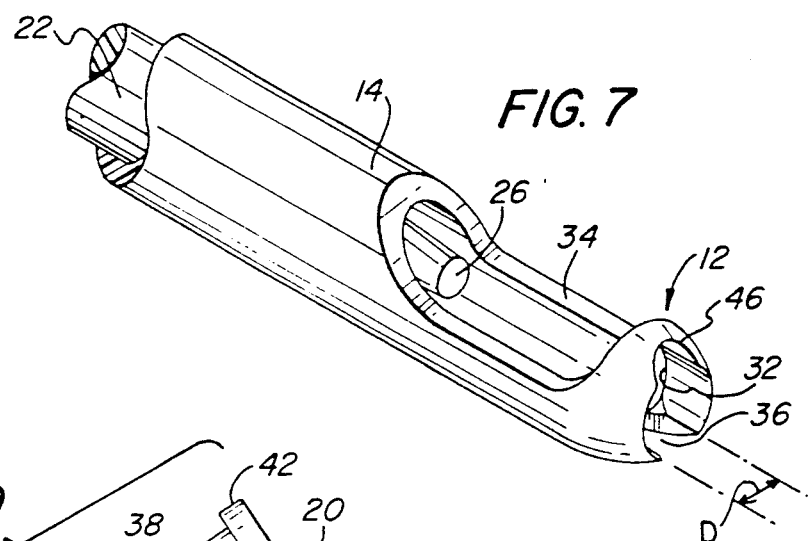
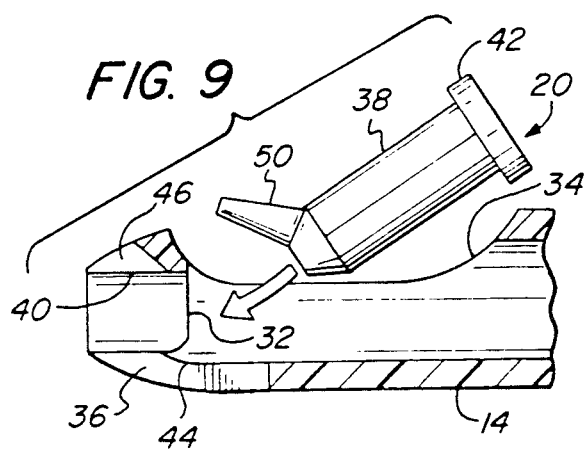
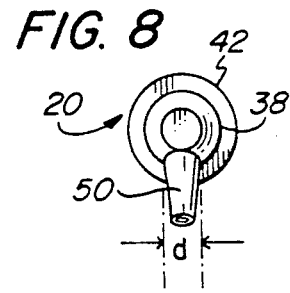
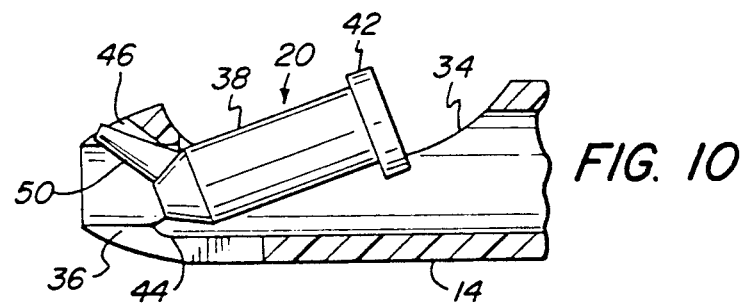
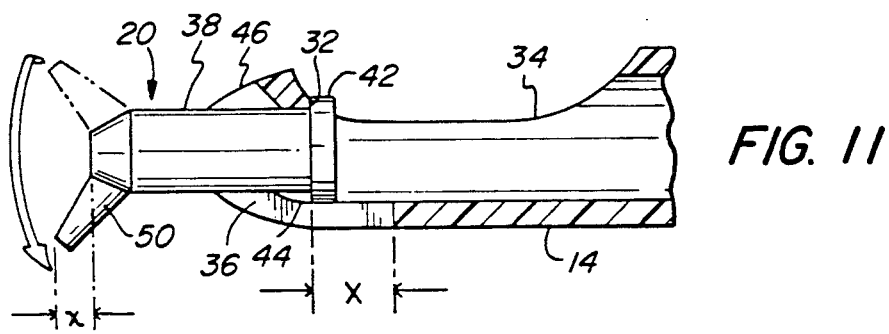

EASY LOADING MANUAL EXTRUDER FOR VISCOUS MATERIAL

FIELD OF THE INVENTION

This invention relates generally to a device for the placement of dental materials, and more particularly to a dental syringe device having an improved barrel front portion facilitating easy loading.

BACKGROUND OF THE INVENTION

As the dental practice advances with the discovery of new filling materials, there developed a need for a new system to place such materials in a tooth. The earliest known delivery system for use with composite resin type dental materials is disclosed in U.S. Pat. No. 3,581,399 issued to Dragan on Jun. 1, 1971. Therein disclosed is a manual extruder for positioning viscous dental material within a prepared tooth. A further improved delivery system is disclosed in U.S. Pat. No. 4,198,756 to Dragan dated Apr. 22, 1980. The device disclosed therein provides a mechanical advantage for the controlled dispensing of the viscous dental material. These devices permit improved dental filling techniques, in that the viscous material is placed in the tooth cavity from the bottom up. This results in the elimination of voids in the tooth filling, which occurred in the previous technique of using a spatula to pack the viscous dental material from the exterior to the interior of the tooth.

As might be expected, refinements have been made to the initial concepts disclosed in the above mentioned Dragan patents. One such refinement is disclosed in U.S. Pat. No. 4,295,828 issuing to Rudler on Oct. 20, 1981. Therein disclosed is a manual extruder very similar to the initial Dragan U.S. Pat. No. 4,198,756, but differing therefrom in that the front end of the barrel is provided with a hinging section for loading and locking a cartridge in place at the front end of the barrel.

It was recognized early on that a syringe having a barrel construction with a snap fit front end construction would facilitate the positioning of a cartridge in the front end so as to provide for easy and rapid placement of a cartridge in the syringe device. Such snap fit front end barrel constructions are disclosed in U.S. Pat. Nos. 3,076,455 and 3,220,412 to McConnaughey dated Feb. 5, 1963 and Nov. 1965 respectively. McConnaughey teaches a syringe device with a snap fit to hold a cartridge onto the end of a barrel by lateral movement relative to a side opening that is accomplished by momentarily distorting the holder to widen the side opening through which the cartridge is inserted to provide the pressed or snap fit. McConnaughey, in the U.S. Pat. No. 3,076,455, FIG. 12 thereof, also discloses a snap fit channel 80 having an internal groove or depression 82 for receiving the flange or bead 78 of the cartridge to retain the cartridge at the front end of a barrel portion and to prevent axial displacement of the cartridge. Brazilian patent application MU5701465 filed Nov. 22, 1977 and published Jul. 3, 1979 discloses a similar "snap or pressed" fit front end construction. The snap fit with undercut groove for retaining a cartridge as applied to a manual extruder for dental materials are thus well known. Such snap fit front end barrel constructions have also been utilized in other dental syringe devices as disclosed in U.S. Pat. No. 4,330,280 and U.S. Pat. No. 4,384,853. These latter two U.S. patents disclose a manually operable dental syringe for a cartridge containing dental material similar to the dental syringe of U.S. Pat. No. 4,198,756, but utilizing a front end barrel construction having a snap fit as suggested by McConnaughey. The snap fit construction disclosed in said latter two patents is provided with an undercut groove to receive the flanged end of the cartridge wherein the sidewalls of the groove at the upper edges have limited flexibility and are spaced apart slightly less than the diameter of the cartridge flange to effect a limited snap connection of the cartridge flange within the undercut groove of the holder.

While these modifications attempted to facilitate the easy placement of a cartridge in a manual extruder, problems with respect thereto have been noted. For example, the inherent flexibility necessary to provide for a snap fit to facilitate attachment of a cartridge, e.g. as disclosed in U.S. Pat. Nos. 4,330,280 and 4,384,853, results in the susceptibility of the side walls of the snap fit compartment or groove to be forcibly spread apart during use if an excessive pressure is applied during an extruding operation. This may well cause the cartridge to be literally shot from the barrel during an extruding operation. This is particularly troublesome when very high extruding pressures are required to be applied to extrude the viscous dental material necessary with such dental cartridges. This is caused by the flange of the cartridge acting as a wedge to force the flexible sidewalls of the snap fit front end to unintentionally spread apart sufficient to cause the cartridge to be forced from its compartment or groove. This is particularly undesirable in a dental procedure when the cartridge at the front end of the syringe is placed in the oral cavity. Should such cartridge be dislodged from the syringe, it can be accidentally inhaled or swallowed by the patient, thereby causing serious harm. Also, wear which normally occurs in use may also cause the cartridge to become loosely held by the syringe to result in unintentional separation of the cartridge during an extruding operation.

Therefore, there is a need for a manual extruder as used in dentistry that will permit easy loading with no resulting risk of the cartridge being separated from the syringe, even during excessive extrusion forces.

SUMMARY OF THE INVENTION

The teachings of the present invention provide a dental syringe having a barrel with a front end adapted to receive a cartridge containing viscous material. The cartridge, being of the type having a nozzle angularly disposed from the body portion containing most of the viscous dental material, and a flange at the rear of the body portion. The front end of the syringe being rigid and having a substantially full circumference with a longitudinal slot therein having a lateral width slightly larger than the diameter of the nozzle of the cartridge A shoulder in the bore of the front end of the syringe prevents the flange at the rear of the cartridge from being forced through the front end. Thereby, the shoulder provides a nearly continuous bearing surface for the flange to rest against. The support of the shoulder along the flange is only eliminated along the relatively narrow width of the slot. Additionally, the barrel can be made of a rigid material preventing the possibility of any flexing of the sidewalls and therefore separation of the cartridge from the syringe during high extrusion forces. The slot is positioned such that upon loading of the cartridge, the angularly disposed nozzle can be placed through the slot with the body of the cartridge riding along the barrel and through the opening into position. This slot greatly facilitates the ease of loading a cartridge with an angularly disposed nozzle into the front end of the syringe.

Accordingly, it is an object of the present invention to provide an improved front end of a manual extruder that is easy to load.

It is another object of the present invention to provide a syringe that is safe and greatly reduces the possibility of a cartridge from being separated therefrom during high extrusion forces.

It is an advantage of the present invention that a cartridge having an angularly displaced nozzle can be securely held in a syringe.

It is another advantage of the present invention that the front end of the syringe is not subject to the wear and fatigue that is evidenced after repeated use of a syringe having a snap fit front end, thereby reducing the possibility of the cartridge unintentionally separating from the syringe.

It is a feature of the present invention that a slot is provided for receiving and guiding the nozzle of a cartridge.

It is another feature of the present invention that a rigid substantially full circle front end with a large shoulder area is used.

These and other objects, advantages, and features will become more readily apparent in view of the following more detailed description.

BRIEF DESCRIPTION OF THE DRAWINGS

FIG. 1 is a side elevational view of the present invention.

FIG. 2 is a perspective view of the top barrel portion of the present invention.

FIG. 3 is a perspective view from the bottom of the barrel portion of the present invention.

FIG. 4 is a cross section of a portion of the barrel of the present invention illustrating the placement of a cartridge.

FIG. 5 is a cross section of a portion of the front barrel of the present invention illustrating a cartridge placed partially therein.

FIG. 6 is a cross section of a portion of the front barrel of the present invention illustrating a cartridge in position for extrusion.

FIG. 7 is a perspective view of another embodiment of the present invention illustrating the front barrel portion.

FIG. 8 is a front elevational view of a cartridge that can be used with the present invention.

FIG. 9 is a cross section of a portion of the front barrel of another embodiment of the present invention illustrating the placement of a cartridge thereon.

FIG. 10 is a cross section of a portion of the front barrel of another embodiment of the present invention illustrating a cartridge placed partially therein.

FIG. 11 is a cross section of a portion of the front barrel of another embodiment of the present invention illustrating a cartridge in position for extrusion.

DETAILED DESCRIPTION OF THE PREFERRED EMBODIMENTS

Figure 12:
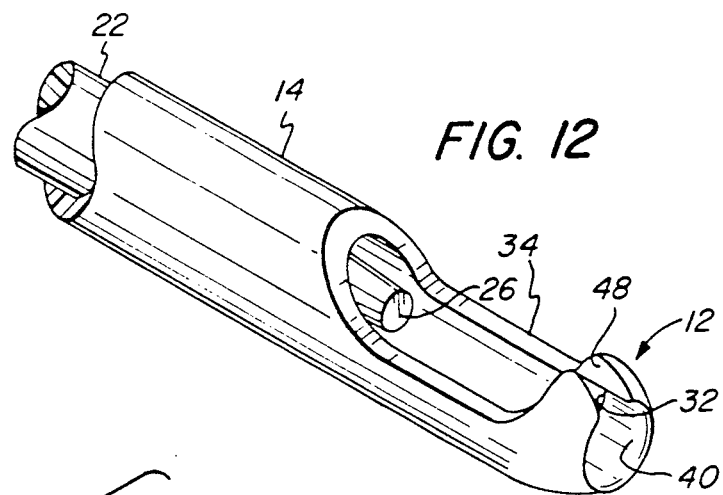
FIG. 12 is a perspective view of another embodiment of the present invention.

FIG. 1 illustrates the application of the present invention. In FIG. 1, a syringe is illustrated generally as 10. The front end or nose is illustrated generally as 12, and the cartridge containing the dental material is illustrated generally as 20. The syringe 10 is comprised of a pivoting handle 18 attached to a finger grip handle 16. A barrel 14 extends through the finger grip handle 16. A plunger slidably extends within the interior bore 24 of the barrel 14. Plunger 22 is advanced forward upon contact with pivoting handle 18. When pivoting handle 18 is squeezed closer to finger grip handle 16, the plunger head 30 slides along the interior surface of pivoting handle 18. The plunger 22 is biased outward by spring 28. The plunger 22 positioned within bore 24 has a plunger tip 26 at the end adjacent the front end or nose 12. As the plunger tip 26 is advanced, a plug, not shown, within the body portion 38 of cartridge 12 is advanced to extrude material from nozzle 50. The body portion 38 of cartridge 20 has a flange 42 at the rear thereof. Flange 42 prevents the cartridge 20 from being forced through the front end 12 by a shoulder 32 circumscribing the interior surface of the front end of bore 40. The cartridge 20 can be positioned within the barrel 14 through breach opening 34. The positioning of the cartridge 20 within the front end or nose 12 of barrel 14 is facilitated by slot 36. Slot 36 extends from the front open end of front end or nose 12 backwards toward the handle beyond the forward end of the breech opening 34. The slot 36 is only wide enough to permit the nozzle 50 to pass therethrough. The body 38 of cartridge 20 does not pass through the slot 36

In FIG. 2, the slot 36 in the front end 12 of barrel 14 can more easily be seen. FIG. 3 illustrates the slot viewing up from the bottom of the barrel 14. One end of shoulder 32 can more clearly be seen in FIG. 3. The shoulder 32 will extend the entire circumference of the interior bore 40 except for the small portion over which slot 36 extends.

FIGS. 4-6 clearly illustrate the advantage the slot serves in facilitating easy loading of the cartridge 20. In FIG. 4, the cartridge 20 can be seen entering breach opening 34. Breech opening 34 is sufficiently long to permit the entire length of the cartridge 20 to pass therethrough. As seen in FIG. 5, upon passing through breech opening 34, the nozzle 50 is permitted to pass through slot 36. However, slot 36 is not wide enough to permit the body 38 to pass through. Therefore, body 38 cannot extend below the top surface of slot 36 along the barrel bore 24 and the front end bore 40. In FIG. 6, the cartridge 20 can be seen in the most forward position ready for extruding of the dental material contained therein. Flange 42 is abutting the shoulder 32. The entire circumference of the front end bore 40, with the exception of the narrow slot 36 width, contains the shoulder thereon. This securely holds cartridge 20. Therefore, the cartridge 20 is prevented from accidentally separating from the syringe 10, even when very large forces are used to extrude the dental material contained within cartridge 20, and even after the syringe 10 has been used numerous times which may cause fatigue or wearing of the restraining surfaces of a snap fit type loading system.

FIG. 7 illustrates another embodiment of the present invention. In addition to the slot 36 on the bottom portion of barrel 14, there is a notch 46 on the top surface thereof. Notch 46 does not extend as far back longitudinally as slot 36. Additionally, in FIG. 7, slot 36 is illustrated having a lateral width D.

FIG. 8 illustrates the front view of a cartridge 20. The nozzle 50 is illustrated having a width of d. The width d of the nozzle 50 is slightly less than the width D of slot 36 illustrated in FIG. 7. The body portion 38 can be clearly seen in FIG. 8 as being substantially larger than the width d of nozzle 50. Therefore, the body portion 38 of cartridge 20 will not pass through slot 36 illustrated in FIG. 7.

FIGS. 9, 10, and 11 illustrate the placement of the cartridge 20 within the improved front end 12 of the barrel 14 of the present invention. In FIG. 9, the cartridge 20 can be placed through the breech opening 34 with the nozzle 50 pointed upward. The nozzle 50, when pointed upward, fits within notch 46 as illustrated in FIG. 10. The cartridge 20 can then be slid forward as illustrated in FIG. 11, so that flange 42 of cartridge 20 will abut shoulder 32. The nozzle 50 can then be rotated to any angular position desired.

FIGS. 9, 10 and 11 additionally illustrate a modification to slot 36. The modification to slot 36 includes a ramp 44, which is a smooth, molded track providing a transition area at the shoulder so as to prevent the body portion 38 of cartridge 20 from catching or hanging up on the shoulder 32 as it is advanced forward into position. This ramp or groove 44 aids in easily sliding the cartridge 20 into the front end portion of barrel 14. Therefore, in the embodiment illustrated in FIGS. 7-11, the cartridge 20 can be placed with either the nozzle 50 pointing up and entering notch 46, or with the nozzle pointed down and entering slot 36.

FIG. 11 provides some indication of a possible length for slot 36. The length of the slot 36 may vary from a short to long longitudinal length, provided only that the nozzle 50 is permitted to easily pass therethrough upon entering the breech opening 34 for easy insertion of the cartridge 20 into the front end of barrel 14. However, the slot 36 is illustrated in FIG. 11 as having a length extending backward from the shoulder 32, a distance X. However, the slot 36 may end forward of the breech opening 34 up to a distance x therefrom. The distance x is illustrated as the axial distance between the discharge end of nozzle 50 and the end of body portion 38 adjacent the nozzle 50. Thereby, when the cartridge 20 is placed within breech opening 34 so that the body portion 38 just clears the front end of breech opening 34, the slot 36 will be positioned sufficiently far rearward to receive the nozzle 50. Therefore, the longitudinal length of slot 36 may be selected to be long enough to permit easy loading, yet short enough not to compromise the structural integrity of the front end of barrel 14. In some applications the slot 36 may extend a short distance from the open end of barrel 14. The slot 36 may not necessarily extend to or past the shoulder 32.

FIG. 12 illustrates yet another embodiment of the present invention. In FIG. 12, there is a channel 48. Channel 48 extends from the end of barrel 14 rearward into the breech opening 34. The channel 48 has a width sufficient to permit nozzle 50 to pass therethrough, yet prevent body portion 38 from passing therethrough.

Figure 13:
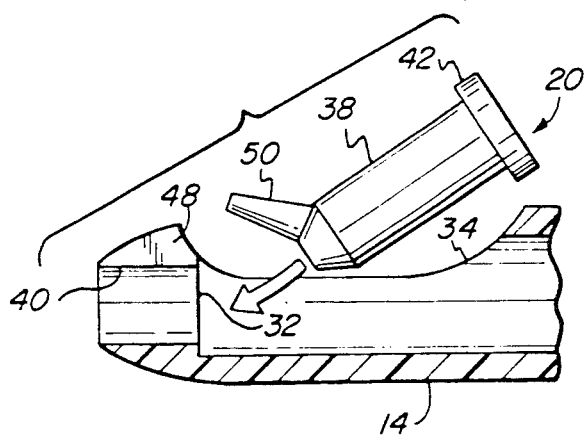
FIG. 13 is a cross section of a portion of the front barrel of another embodiment of the present invention illustrating the placement of a cartridge therein.
Figure 14:
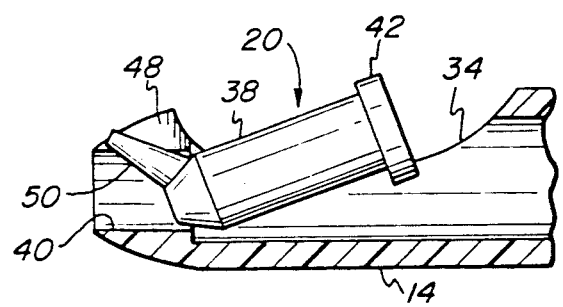
FIG. 14 is a cross section of a portion of the front of the barrel of another embodiment of the present invention illustrating cartridge placed partially therein.
Figure 15:
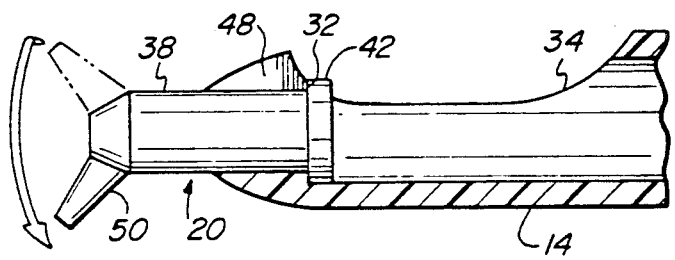
FIG. 15 is a cross section of a portion of the front barrel of another embodiment of the present invention illustrating a cartridge in position for extrusion.

FIGS. 13, 14 and 15 illustrate the insertion of a cartridge 20 into the front end portion of barrel 14. In this embodiment, the nozzle 50 is inserted while pointed upward. The nozzle can easily be slid forward through front end bore 40 until the rear flange 42 abuts shoulder 32. The cartridge 20 can then be rotated in any desired position as illustrated in FIG. 15.

The embodiments of the present invention illustrated above, incorporating a slot, notch, or channel, greatly facilitates the loading of a cartridge having an angularly disposed nozzle into the front end of a manual extruder. This is accomplished while providing very secure containment of the cartridge within the syringe, even during very high extrusion forces. This improves the safety of the device, especially when used in confined areas, such as an oral cavity in dentistry. The potentially fatal consequences of a tip becoming unintentionally separated from the syringe during operation within an oral cavity of a dental patient, is virtually eliminated with the present invention.

Although the preferred embodiment has been illustrated and described, it will be obvious to those skilled in the art that various modifications may be made without departing from the spirit and scope of this invention.

We claim:

1. A manual extruder for use with a cartridge having a body portion, a laterally circumscribing flange at one end thereof and a connected angularly disposed discharge nozzle comprising:
   a barrel having a front end and a rear end,
   said front end terminating in a front opening through which the body of the cartridge is adapted to extend,
   an internal shoulder disposed adjacent said front opening,
   a side breech opening for receiving a cartridge formed in said barrel spaced rearwardly of said front opening,
   a longitudinal slot extending along said front end of said barrel to said front opening, said slot being angularly disposed relative to said side breech opening and
   said slot having a lateral width sufficient for accommodating a cartridge discharge nozzle only when a cartridge is inserted in said breech opening,
   and a plunger slidably mounted in said barrel,
   said plunger extending beyond the rear end of said barrel.

2. A manual extruder as in claim 1 further comprising:
   handle means, attached to said barrel and contacting said plunger, for providing a mechanical advantage in advancing said plunger.

3. A manual extruder as in claim 2 wherein:
   said slot is positioned in the bottom portion of said barrel as held by said handle means.

4. A manual extruder as in claim 1 wherein:
   said barrel has a notch adjacent the front end opposite the longitudinal slot.

5. A manual extruding system for use with a viscous material comprising:
   a barrel, said barrel having a front end terminating in a front opening and a rear end, said barrel having a longitudinal slot extending to said front opening;
   a side breech opening formed in said barrel adjacent to and spaced rearwardly of said front end;
   said slot having its axis angularly disposed relative to the axis of said breech opening, a cartridge adapted to fit through said breech opening, said cartridge having a body portion and an angularly disposed nozzle, said body portion having a diameter larger than said nozzle diameter, said body diameter being larger than the lateral width of said slot, said cartridge having a flange;

a shoulder circumscribing a portion of the internal circumference of said barrel at the front end for preventing the flange from passing therethrough;

a plunger slidably mounted within said barrel; and handle means, attached to said barrel and contacting said plunger, for providing a mechanical advantage in advancing said plunger, whereby a cartridge having an annular disposed nozzle can be inserted through said side breech opening and securely held within said barrel.

6. A manual extruding system as in claim 5 further comprising:

ramp means forming a transition area at said shoulder adjacent said slot, for facilitating guiding said body portion of said cartridge along the surface of said barrel to past said shoulder.

7. A manual extruding system for use with a viscous material comprising:

a barrel, said barrel having a front and rear end, said barrel having a longitudinal slot adjacent the front end;

a breech opening adjacent the front end;

a cartridge adapted to fit within said breech opening, said cartridge having a body portion and an angularly disposed nozzle, said body portion having a diameter larger than said nozzle diameter, said body diameter being larger than the lateral width of the slot, said cartridge having a flange;

a shoulder circumscribing a portion of the internal circumference of said barrel at the front end preventing the flange from passing therethrough;

a plunger slidably mounted within said barrel; and handle means, attached to said barrel and contacting said plunger, for providing a mechanical advantage in advancing said plunger, whereby a cartridge having an angular disposed nozzle can be easily placed and securely held within said barrel, wherein said slot is opposite said breech opening.

8. A manual extruding system as in claim 7 wherein:
said slot comprises an extension of said breech opening adjacent the front end.

9. A manual extruding system as in claim 8 wherein:
said channel is positioned on the top of said barrel when held by said handle means.

10. A manual extruding system as in claim 7 wherein:
said slot is positioned at the bottom when held by said handle means.

11. A manual extruding system for use with a viscous material comprising:

a barrel, said barrel having a front and rear end, said barrel having a longitudinal slot adjacent the front end;

a breech opening adjacent the front end;

a cartridge adapted to fit within said breech opening, said cartridge having a body portion and an angularly disposed nozzle, said body portion having a diameter larger than said nozzle diameter, said body diameter being larger than the lateral width of the slot, said cartridge having a flange;

a shoulder circumscribing a portion of the internal circumference of said barrel at the front end preventing the flange from passing therethrough;

a plunger slidably mounted within said barrel; and handle means, attached to said barrel and contacting said plunger, for providing a mechanical advantage in advancing said plunger, whereby a cartridge having an angular disposed nozzle can be easily placed and securely held within said barrel, and a notch in the front end of said barrel opposite said slot and extending a shorter longitudinal distance than said slot.

12. A manual extruding system for use with dental materials comprising:

a front handle;

a back handle pivotally connected to said front handle;

a barrel, said barrel having a front and rear end, said rear end attached to said front handle;

said barrel having a breech opening adjacent said front end, said front end having a shoulder circumscribing a portion of the interior diameter thereof, said barrel having a slot therein on the surface opposite the breech opening, and a notch in said front end in line with said breech opening and opposite said slot;

a cartridge having an angularly disposed nozzle adapted to fit within said breech opening, said cartridge having a body portion with a diameter larger than the lateral width of said slot;

a flange attached to one end of said cartridge, said flange having a bearing surface adapted to mate with said shoulder;

ramp means adjacent said slot to provide a transition area for facilitating guiding the body of said cartridge along the slot and past said shoulder; and a plunger contacting said back handle adapted to slide within said barrel and whereby a cartridge containing viscous material can be easily placed within said barrel, yet be securely held.

* * * * *